United States Patent
Kim et al.

(10) Patent No.: US 8,293,271 B2
(45) Date of Patent: Oct. 23, 2012

(54) ENCAPSULATED MATERIALS AND METHODS FOR ENCAPSULATING MATERIALS

(75) Inventors: Kyekyoon Kim, Champaign, IL (US); Hyungsoo Choi, Champaign, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 184 days.

(21) Appl. No.: 12/481,394

(22) Filed: Jun. 9, 2009

(65) Prior Publication Data

US 2009/0304788 A1 Dec. 10, 2009

Related U.S. Application Data

(60) Provisional application No. 61/060,256, filed on Jun. 10, 2008.

(51) Int. Cl.
*A61K 9/48* (2006.01)
*A61K 35/12* (2006.01)

(52) U.S. Cl. .......... 424/455; 424/93.7; 424/184.1; 264/4; 426/72; 426/235; 426/74

(58) Field of Classification Search .......... 427/483; 428/402, 402.2, 402.21; 424/455, 93.7, 184.1, 424/497, 489, 501, 490, 491, 492, 494; 141/173; 128/200.14; 425/5; 264/4, 4.1

See application file for complete search history.

(56) References Cited

U.S. PATENT DOCUMENTS

| | | | | |
|---|---|---|---|---|
| 5,135,759 | A * | 8/1992 | Johnson | 424/561 |
| 5,639,467 | A * | 6/1997 | Dorian et al. | 424/422 |
| 6,214,300 | B1 * | 4/2001 | Morrison et al. | 422/238 |
| 6,989,169 | B2 * | 1/2006 | Ripoll et al. | 426/235 |
| 2002/0007869 | A1 * | 1/2002 | Pui et al. | 141/173 |
| 2005/0123614 | A1 * | 6/2005 | Kim et al. | 424/489 |
| 2007/0296099 | A1 * | 12/2007 | Larsen et al. | 264/4.1 |

* cited by examiner

*Primary Examiner* — James J Seidleck
*Assistant Examiner* — S. Camilla Pourbohloul
(74) *Attorney, Agent, or Firm* — Guntin Meles & Gust, PLC; Andrew Gust

(57) ABSTRACT

A system that incorporates teachings of the present disclosure may include, for example, an apparatus having an outer nozzle operable to discharge an outer stream of a shell solution, and an inner nozzle operable to discharge an inner stream of a core solution intermixed with a plurality of materials. The outer stream can substantially surrounds the inner stream, thereby forming a combined stream. A plurality of capsules can be formed responsive to a force applied to the combined stream. At least a portion of the plurality of capsules are desirable capsules, each having a core encapsulated by a portion of the shell solution. The core can have at least one of the plurality of materials encapsulated by a portion of the core solution without protruding an outer surface of the portion of the shell solution. Additional embodiments are disclosed.

20 Claims, 6 Drawing Sheets

ENCAPSULATED MATERIALS AND METHODS FOR ENCAPSULATING MATERIALS

PRIOR APPLICATION

The present application claims the benefit of priority to U.S. Provisional Application No. 61/060,256 filed on Jun. 10, 2008, by Kim et al., entitled "Encapsulated Materials and Methods for Encapsulating Materials." All sections of the aforementioned application are incorporated herein by reference.

FIELD OF THE DISCLOSURE

The present disclosure relates to the field of materials and material preparation or processing. Embodiments of the disclosure relate to encapsulated materials and methods or processes for encapsulating materials such as cellular materials.

BACKGROUND

Cell therapy can depend upon the ability to provide cells to a recipient while restraining the recipient's immune response from rejecting the cells. One example of providing these cells has been to provide cells while attempting to prohibit the immune response to the cells themselves and limit the immune response to any associated materials. In the past, attempts have been made to provide encapsulated cells that would protect the cell from initiating the host's immune response. However, portions of the cell have often remained exposed, unencapsulated, and/or antigenic. The exposed portions can extend beyond the encapsulate wall, thereby initiating the immune response.

DETAILED DESCRIPTION

Figure 1:
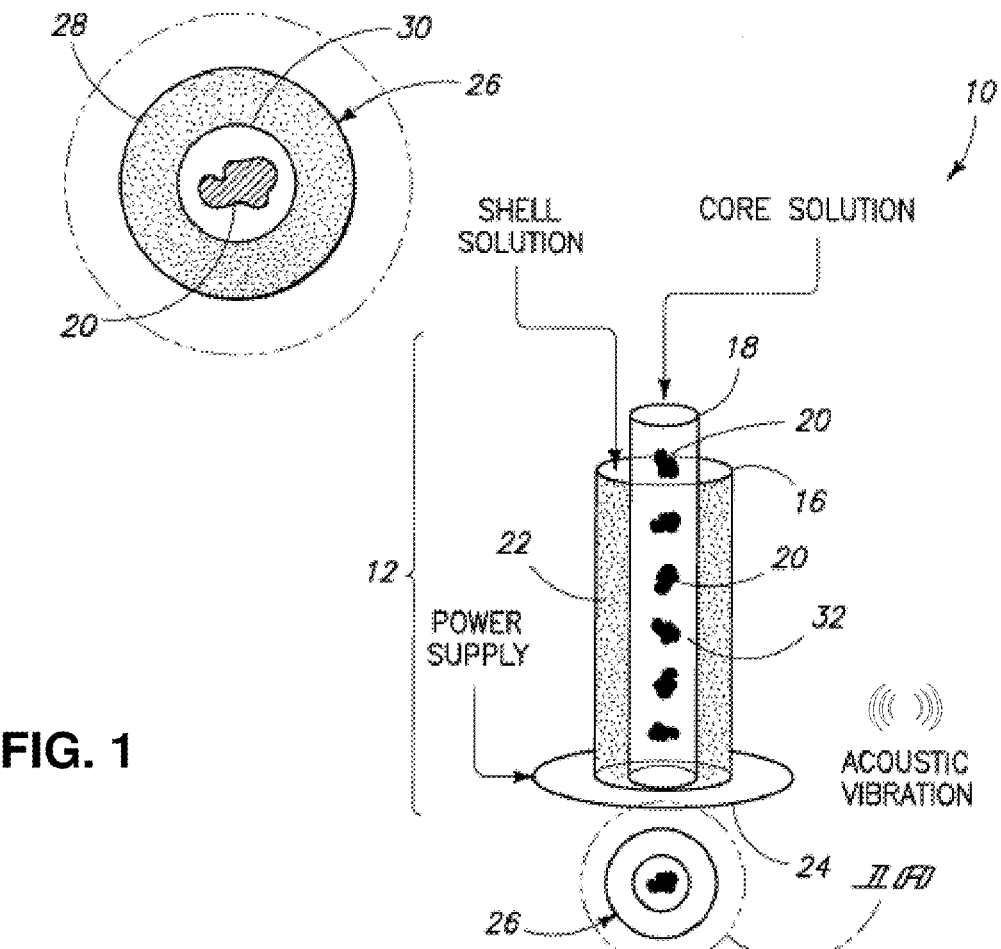
FIG. 1 depicts an illustrative embodiment of an encapsulating apparatus.
Figure 1:
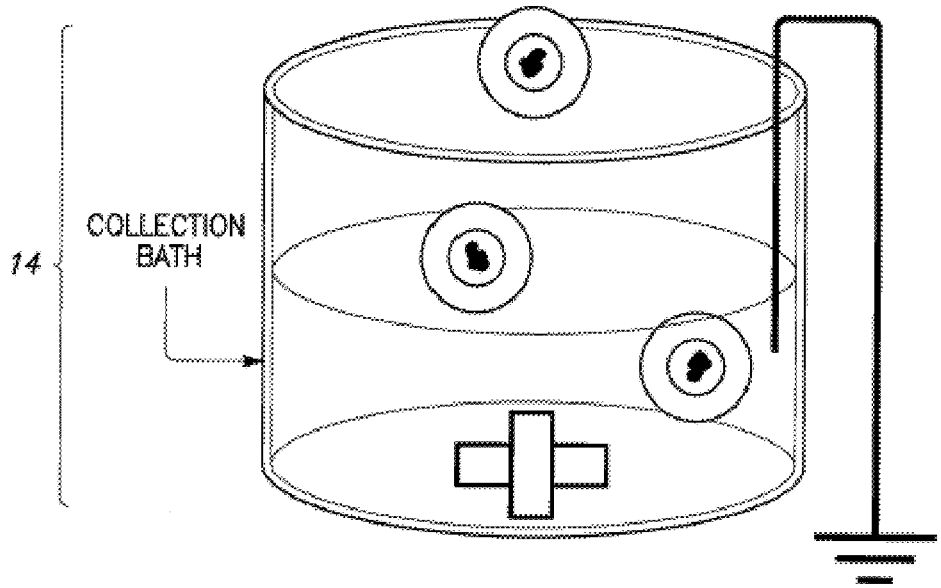

One embodiment of the present disclosure entails an apparatus having an outer nozzle operable to discharge at an egress of the outer nozzle an outer stream at a first flow rate, the outer stream comprising a shell solution, and an inner nozzle placed within the outer nozzle, wherein the inner nozzle is operable to discharge at an egress of the inner nozzle an inner stream at a second flow rate, the inner stream comprising a core solution intermixed with a plurality of materials. The outer stream can substantially surrounds the inner stream, thereby forming a combined stream. A plurality of capsules can be formed responsive to a force applied to the combined stream. At least a portion of the plurality of capsules are desirable capsules, each having a core encapsulated by a portion of the shell solution. The core can have at least one of the plurality of materials encapsulated by a portion of the core solution. The at least one material in the core does not protrude an outer surface of the portion of the shell solution.

One embodiment of the present disclosure entails applying a force to a combined stream to produce a plurality of capsules. The combined stream can have an inner stream with a core solution intermixed with a plurality of materials, and an outer stream of a shell solution. At least a portion of the plurality of capsules are desirable capsules, each comprising a core encapsulated by a portion of the shell solution. The core can have at least one of the plurality of materials encapsulated by a portion of the core solution, whereby the at least one material in the core does not protrude an outer surface of the portion of the shell solution.

One embodiment of the present disclosure entails applying a plurality of capsules to a patience to reduce or eliminate a disease of the patient. The plurality of capsules can be produced by an apparatus that applies an acoustic force to a combined stream. The combined stream can have an inner stream including a core solution intermixed with a plurality of mammalian cells, and an outer stream including a non-antigenic solution. Each of the plurality of capsules can include a core encapsulated by a portion of the non-antigenic solution. The core can have at least one of the plurality of mammalian cells encapsulated by a portion of the core solution, whereby the at least mammalian cell in the core does not protrude an outer surface of the portion of the non-antigenic solution.

One embodiment of the present disclosure entails producing a plurality of capsules from a dual stream excited by a force. At least a portion of the plurality of capsules are desirable, each having a core surrounded by an outer shell, whereby the core does not protrude an outer surface of the outer shell. In one embodiment the core can correspond to a mammalian cell.

One embodiment of the present disclosure entails a computer-readable storage medium having computer instructions to manage operations of the aforementioned apparatus to produce the plurality of capsules according to any combination of the foregoing embodiments.

One embodiment of the present disclosure entails a computer-readable storage medium having computer instructions to direct a device that applies the plurality of capsules on a portion of a mammal as medicinal treatment. The capsules applied to the mammal can have any combination of the aforementioned embodiments.

The apparatus and methods provided herein will be described with reference to FIGS. 1-9. Referring first to FIG. 1, an apparatus 10 is provided that includes a coaxial dual-nozzle apparatus 12 orientated in relation to a receiving reservoir 14. Coaxial dual-nozzle apparatus 12 can include an outer nozzle 16 having an inner tube 18 therein. Apparatus 12 can be configured to encapsulate a core within a shell.

Outer nozzle 16 can receive a shell solution 22, and inner nozzle 18 can receive a core solution 32. Either or both the shell solution 22 and core solution 32 can be comprised of polymeric or metallic compositions and can have equal or different concentrations. Core solution 32 can contain material 20 to be encapsulated such as cells, for example. The shell and core solutions can comprise a variety of materials depending on the resulting capsule application including polymers and metals. Upon application of forces such as electrostatic, gas dynamic, fluid dynamic and/or acoustic forces of the two solutions, a uniform capsule 26 can be formed at the terminal end of apparatus 12.

In accordance with example implementations, acoustic excitation may be utilized to form capsule 26. Capsule 26 can include material 20 surrounded by core 30. Core 30 can also be surrounded by shell 28. Capsule 26 can be produced and provided to reservoir 14. Between reservoir 14 and apparatus 12 a power supply can be configured to electrically charge the capsules exiting the terminal end of apparatus 12 and prevent them from coalescing in the receiving reservoir 14, due to the electrical repulsion between the charged capsules.

Reservoir 14 can be a collection reservoir configured to receive capsule 26 within a solution. Reservoir 14 can also be configured to provide an electrical potential to the solution to prevent or control charge build-up in the reservoir. The solution in the reservoir 14 may contain additives to facilitate gelation or crosslinking or solidification of capsule 26. Additives can include but are not limited to inorganic salts such as $CaCl_2$ and $BaCl_2$. According to example implementations material 20 may be substantially centered within individual capsule 26 or can move about the shell 28 without protruding its outer surface.

Material 20 provided to nozzle 18 and eventually encapsulated within capsule 26 can include biomaterials such as viable or even non-viable biologic materials including but not limited to mammalian cells such as pancreatic islet cells, myoblast cells, iNOS-expressing cells, parathyroid cells, fibroblast cells, hepatocyte cells, and hormone secreting cells having a protein base, for example. The islet cells can be living cells or dormant cells. In example implementations, the cells can be mammalian and isolated from a variety of donors, including but not limited to, porcine, ovine, human, and/or bovine.

Within capsule 26, imaging agents can also be provided that can contain nanoparticles, for example. In addition, the nanoparticles can be utilized for tracing using imaging technology such as Magnetic Resonance Imaging (MRI). Such additives can be radioactive, have dual modality and/or be optical or MRI contrast agents, for example. These contrast agents can be inserted into or solidified within an encapsulated portion of capsule 26, for example.

Capsule 26 can include a shell comprising primarily the material provided to nozzle 16. The shell and/or the core can be an alginate as alginates can be immuno-inert (non-antigenic), biocompatible, and/or have limited degradability. In other implementations, the shell and/or core can comprise a degradable, either fully or partially, material.

In example implementations, the level of cross-linking between the materials of capsule 26 can be controlled. For example, solution 22 can include materials that when capsule 26 is formed the level of bonding and/or interaction between core 30 and shell 28 is predetermined to provide different strength characteristics. These strength characteristics can include degradation and/or density for example. Other materials can be utilized as the shell portion as well. These shell materials can be selected from a variety of materials having physical properties necessitated by application requirements. For example, carbohydrates, synthetic polymers and the like may be utilized as well as materials that are compatible under a given set of application conditions.

Utilizing apparatus 10 materials such as cell and/or imaging agents can be encapsulated and centered to form microcapsules at high production rates. Example implementations can include encapsulated pancreatic islet cell transplantation where the capsules can be made of alginate and can be in the range of 450 to 600 μm in diameter. The microcapsule production rate can exceed 1000 microcapsules per second, for example. According to an example implementation, the capsule can include a cell encapsulated by a core 30 which can be in turn surrounded by a shell 28.

One example application of the present disclosure is to provide entirely encapsulated (i.e., non-antigenic) pancreatic islet cells for the treatment of Type 1 diabetes without or substantially minimizing the use of immunosuppressive drugs. Although the transplantation of pancreatic islet cells is a viable therapy for Type 1 diabetes the current methods have limited effectiveness; resulting in poor insulin control and necessitating the use of immune suppression therapy which restricts the therapy to a limited number of patients. The encapsulation of islet cells in capsules by prior art systems has been shown to be non-antigenic thus overcoming the limitations of the current technology.

According to example implementations, products of the apparatus and methods described herein may be applied without the need of immune suppression. Methods such as those described in K. Y. Jang, K. Kim, and R. S. Upadhye, "Study of sol-gel processing for fabrication of hollow silica-aerogel spheres," J. Vac. Sci. Technol. A, 8:33, pp. 1732-1735, 1990; K. Kim, K. Y. Jang, and R. S. Upadhye, "Hollow silica spheres of controlled size and porosity by sol-gel processing," J. Am. Ceram. Soc., 74:8, pp. 1987-1992, 1991; C. Berkland, K. Kim, and D. W. Pack, "Fabrication of PLG microspheres with precisely controlled and monodisperse size distributions," J. Controlled Release, 73, 59-74, 2001; and Cory Berkland, D. W. Pack, and K. Kim, "Uniform double-walled polymer microspheres of controllable shell thickness," Journal of Controlled Release, vol. 96, no. 1, pp. 101-111, 2004, can be applied to the present disclosure, and the materials utilized therein are incorporated by reference herein.

As an example, the present disclosure provides an apparatus 10 wherein the inner nozzle 18 can carry an islet cell-containing alginate core solution 32 of one concentration, and the outer nozzle 16 another alginate-containing shell solution 22 of equal or different concentrations so that the islet cell-containing core solution stream is at least substantially or completely surrounded by the outer solution stream to form a coaxial jet. This jet, upon unidirectional or omnidirectional acoustic excitation caused by a common acoustic piezoelectric device, can break up the stream into substantially uniform core-shell microcapsules with the islet cell-containing alginate core surrounded by the alginate shell as shown in FIG. 1. By properly selecting the size of the inner and outer nozzle and adjusting the relative flow rates of the inner and outer solution stream and the frequency and amplitude of the acoustic excitation, the size and thickness of the capsules may be precisely controlled to the desired dimensions. In this way, one can provide that the islet cells contained in the microcapsules are separated from the microcapsule wall, at least as much as the thickness of the alginate shell and as a result, the immunoreactions that may be caused after islet cell transplantation by the islet cells protruding from the capsules may not be initiated.

According to example implementations, by flowing the solution of the inner nozzle 18 into the outer nozzle 16 to form the shell one can provide that the cells be contained in the core region of the core-shell microcapsules. Material solidification processes (e.g., crosslinking) can start from the outer surface of the microcapsules and move inward to provide cells that are contained inside the microcapsules away from the outer surface of the microcapsules.

Figure 2:
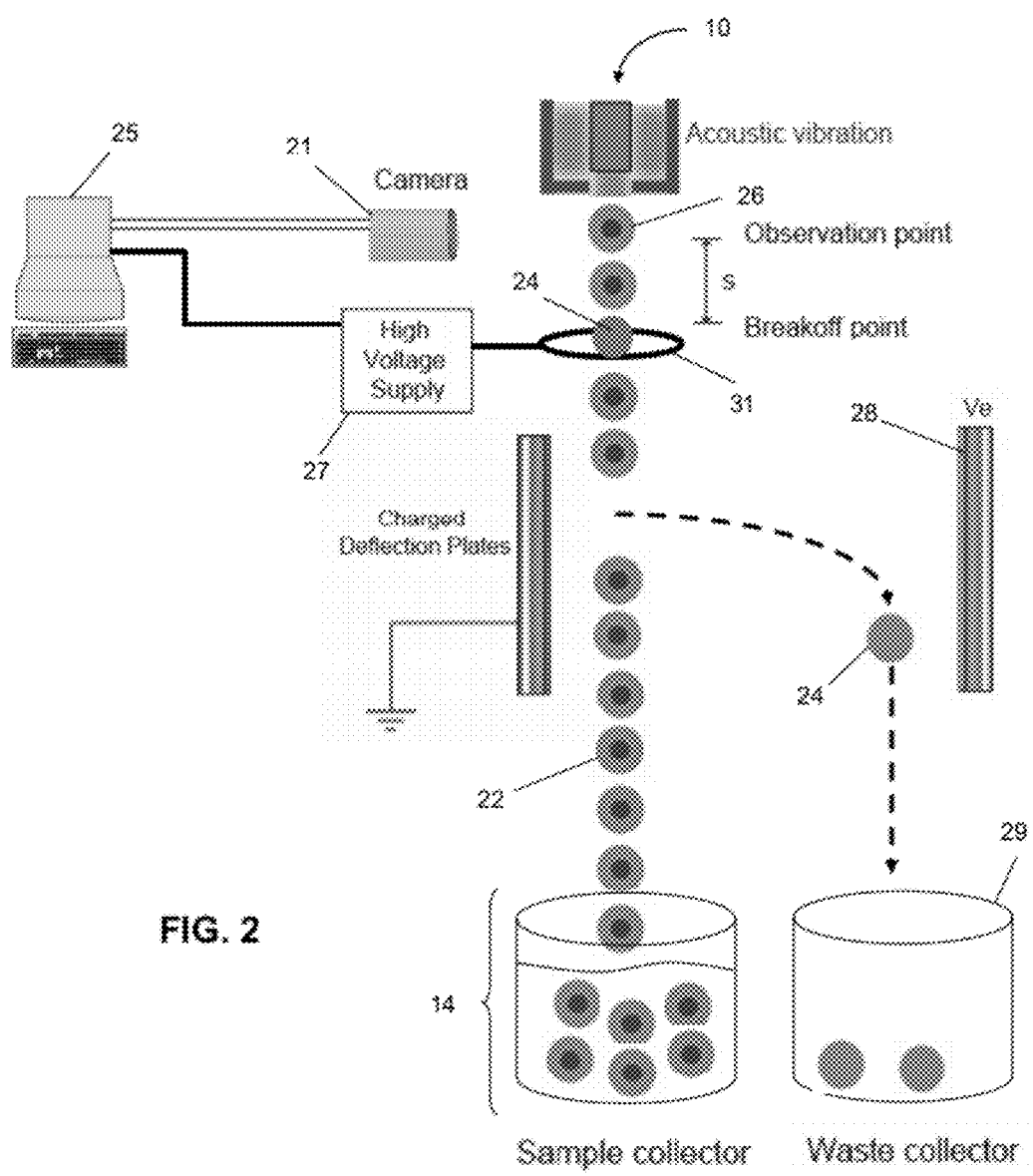
FIG. 2 depicts an illustrative embodiment of the apparatus of FIG. 1 configured to inspect and segregate capsules.

FIG. 2 depicts an illustrative embodiment of the apparatus of FIG. 1 configured to inspect and segregate capsules. Utilizing the apparatus, capsules prepared in accordance with the materials and methods described can be assayed for completeness of encapsulation. A common high resolution camera 21 can provide images to a controller 25 (e.g., a common computing device such as a desktop computer or server) which can utilize common image processing technology to inspect the capsules as they depart apparatus 10. If a capsule is determined to be an undesirable capsule 24 such as missing a core, or having a protruding core, the controller 25 can direct a high voltage source 27 to charge the undesirable capsule 24 by way of a ring conductor 31 with a negative or positive bias.

The bias is only applied to undesirable capsules 24. The controller 25 can then be programmed to direct a deflection plate 28 to segregate the undesirable capsule 24 away from a path of the desirable capsules 22 by utilizing a potential that draws the undesirable capsule 24 towards the plate 28 and redirects the undesirable capsule 24 to a waste collector 29. Since only the undesirable capsules 24 are charged, the desirable capsules 22 are substantially unaffected by the potential of plate 28, thereby maintaining their current path towards a sample collector 14 with a collection solution which may or may not contain additive(s) to facilitate gelation, crosslinking or solidification.

Figure 3:
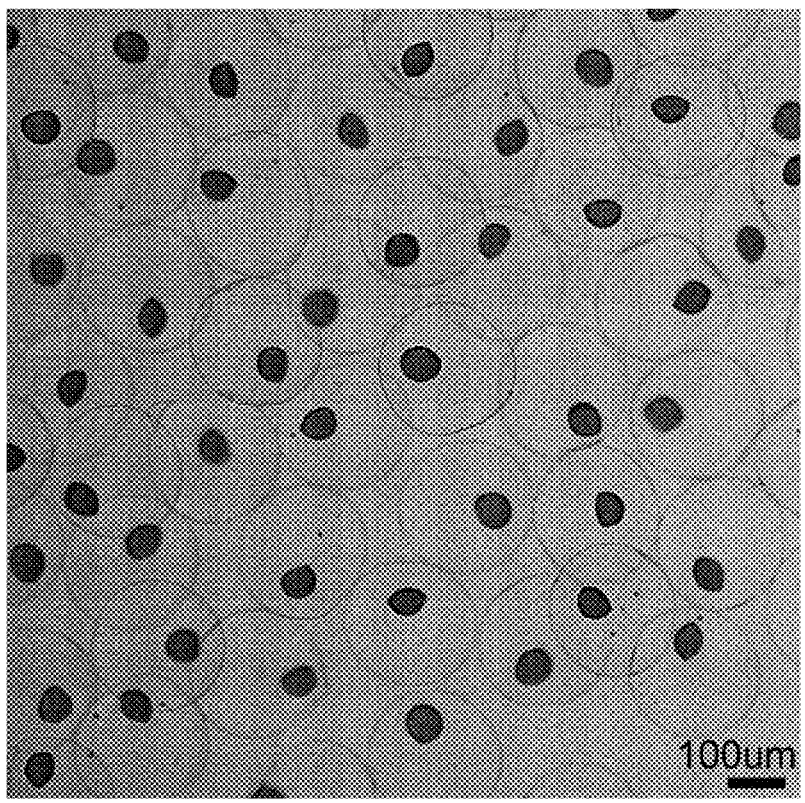
FIGS. 3-7 depicts illustrative embodiments of capsules created by the apparatus of FIG. 1.
Figure 4:
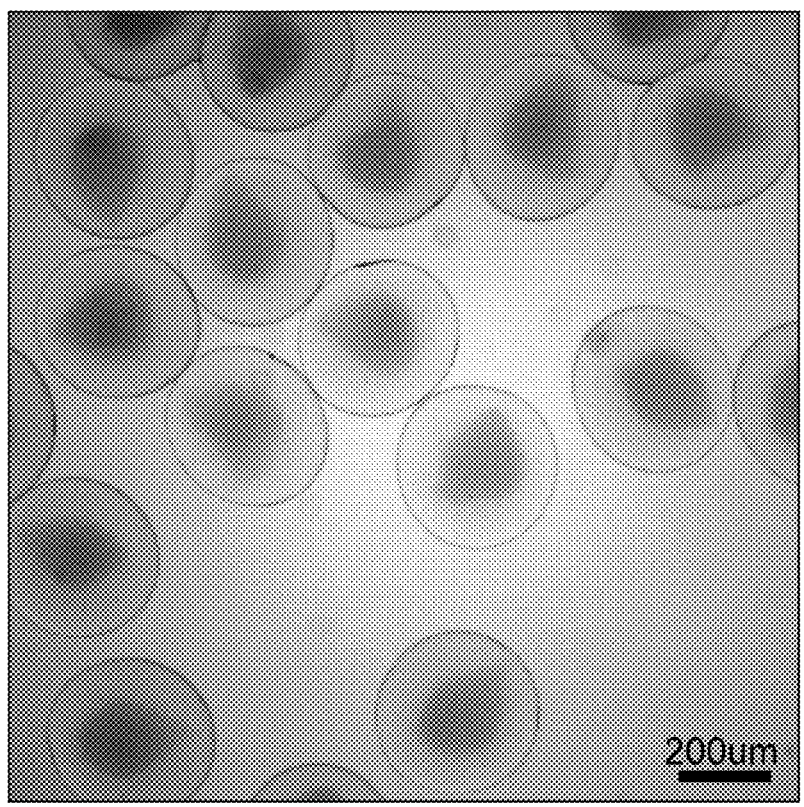

Referring to FIG. 3, thus fabricated alginate microcapsules are shown that contain surrogate cells, i.e., ethyl cellulose in the core region. In this illustration, the shell is rigid while the core can move about the capsule without protruding the outer rigid shell. This depiction can demonstrate that these cells in the core do not extend beyond the perimeter established by the microcapsules and thus the present disclosure is capable of containing the cells in the core region. The present method can provide control of the polymer concentrations and flow rates of the outer and inner solutions, and thus controlling the mass ratios of the two polymers in each nascent droplet, resulting in precise control of the microcapsule diameter and the shell thickness. As a result, the minimum distance between the outer surface of the microcapsule and the cell in the core can be controlled. Likewise, the selection of materials between the inner and outer solutions can be chosen based on porosity of the materials, the porosities giving rise to different densities of the materials.

According to example implementations, an ethyl cellulose core, for example, can be utilized as a surrogate cell using the apparatus 10 of FIG. 1. Capsules can be produced at a rate of about 1000 per second with alginate as the shell material. A similar feasibility test can also be performed with a viscous dextran core rather than an ethyl cellulose core. The capsules produced using the viscouse dextran core with a rigid outer shell is demonstrated in FIG. 4. Microcapsules of the present disclosure can be greater than 400 μm in diameter or from about 500 to 600 μm in diameter. The cells within the shell can be 20 μm in size with a production rate of about 1000 encapsulated cells per second.

Figure 5:
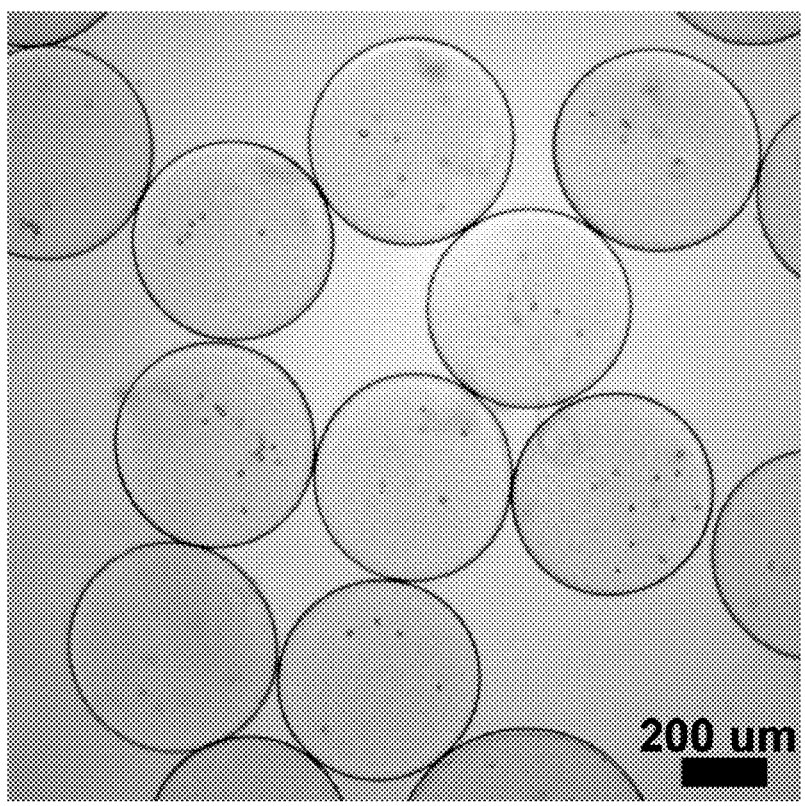
Figure 6:
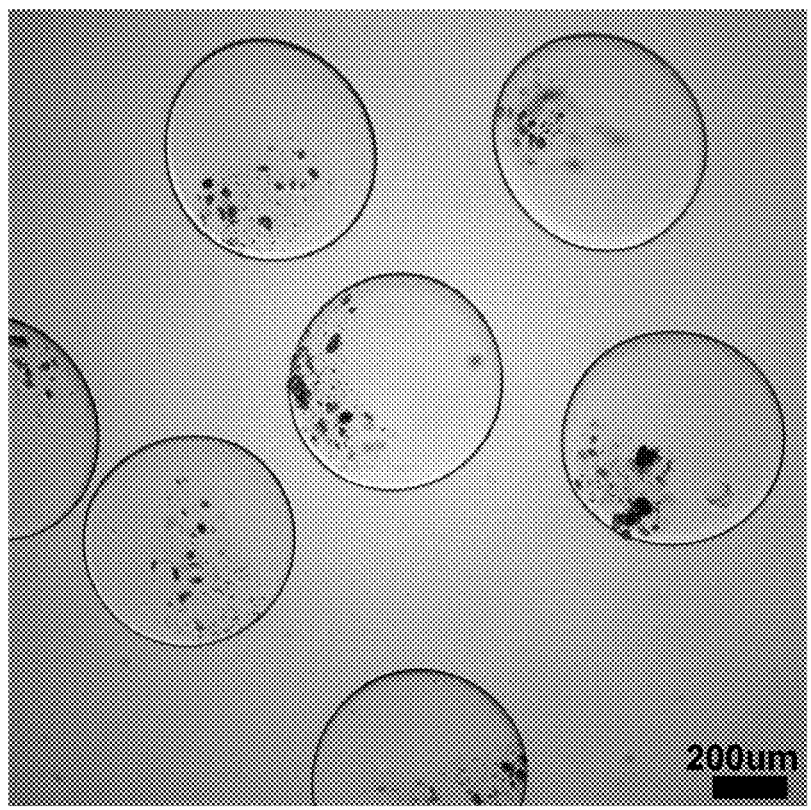
Figure 7:
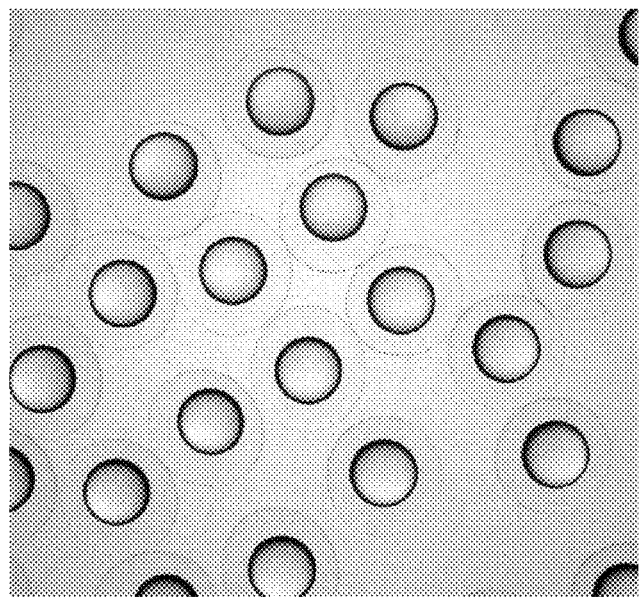

FIGS. 5 and 6 depict optical microscope pictures of alginate capsules encapsulating mice fibroblast cells (FIG. 5) and bovine liver cells (FIG. 6) with a scale bar of 200 μm. In both illustrations the shell thickness is very thin but rigid, thereby preventing the cells contained therein from protruding the outer shell. With a thin outer shell, which can be produced by a controlled exposure to a solidification solution, the cells in the capsule can move about freely without being overly constrained or damaged by an excessively thick rigid shell. FIG. 7 depicts optical microscopic pictures of alginate microspheres encapsulating canola oil and water-soluble dextran with a scale bar is 200 μm. FIG. 7 illustrates the diversity of microcapsules that can be created by the apparatus 10 of the present disclosure.

Figure 8:
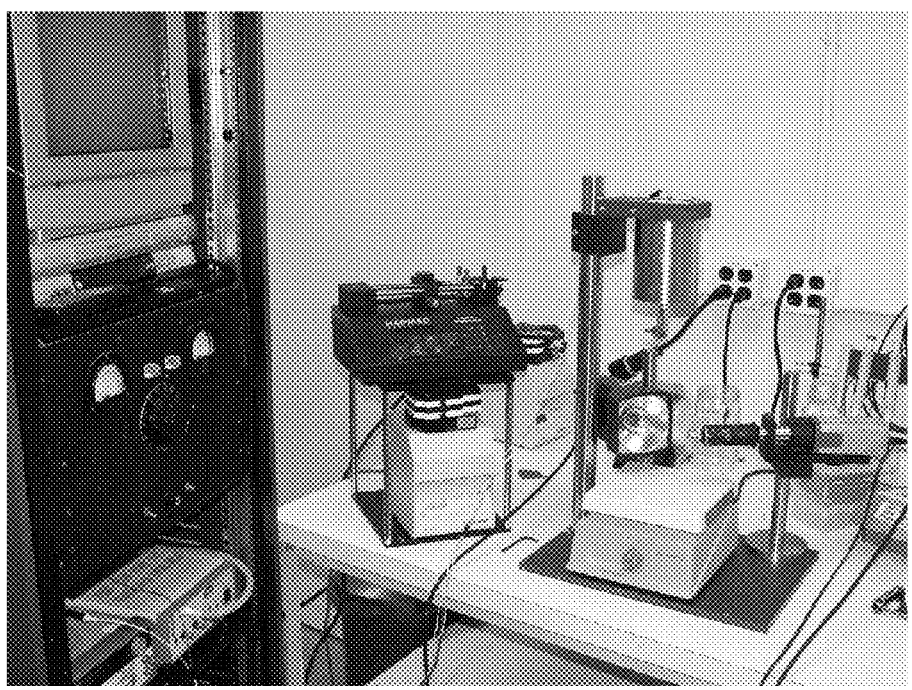
FIG. 8 depicts an illustrative embodiment of the apparatus of FIG. 1 in a laboratory setting.

FIG. 8 depicts apparatus 10 in a laboratory setting utilizing an acoustic wave generator. The apparatus depicted in FIG. 8 has been utilized to produce one or more of the aforementioned capsule embodiments.

From the foregoing descriptions, it would be evident to an artisan with ordinary skill in the art that the aforementioned embodiments can be modified, reduced, or enhanced without departing from the scope and spirit of the claims described below. For example, apparatus 12 may be configured to encapsulate a core within a primarily metal comprising shell and as such, apparatus 12 may be constructed of materials configured to encapsulate using molten metal. Broadly speaking, there can be innumerable combinations of materials and shell solutions for producing capsules by way of the apparatus disclosed herein. For practical reasons these embodiments are not disclosed, but are contemplated by the present disclosure.

Other suitable modifications can be applied to the present disclosure. Accordingly, the reader is directed to the claims for a fuller understanding of the breadth and scope of the present disclosure.

Figure 9:
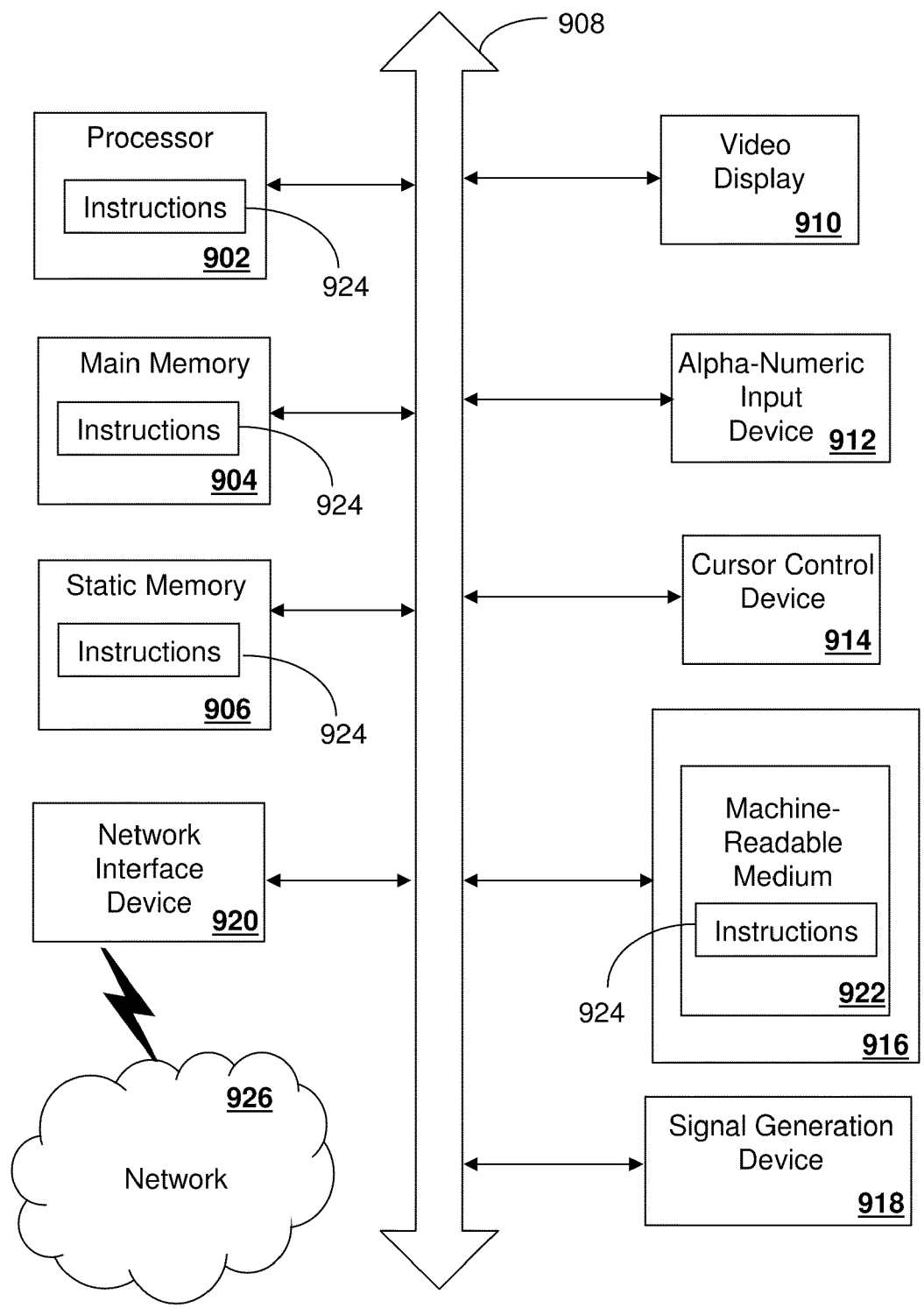
FIG. 9 depicts an illustrative diagrammatic representation of a machine in the form of a computer system within which a set of instructions, when executed, may cause the machine to perform any one or more of the methodologies disclosed herein.

FIG. 9 depicts an exemplary diagrammatic representation of a machine in the form of a computer system 900 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 900 may include a processor 902 (e.g., a central processing unit (CPU), a graphics processing unit (GPU, or both), a main memory 904 and a static memory 906, which communicate with each other via a bus 908. The computer system 900 may further include a video display unit 910 (e.g., a liquid crystal display (LCD), a flat panel, a solid state display, or a cathode ray tube (CRT)). The computer system 900 may include an input device 912 (e.g., a keyboard), a cursor control device 914 (e.g., a mouse), a disk drive unit 916, a signal generation device 918 (e.g., a speaker or remote control) and a network interface device 920.

The disk drive unit 916 may include a machine-readable medium 922 on which is stored one or more sets of instructions (e.g., software 924) embodying any one or more of the methodologies or functions described herein, including those methods illustrated above. The instructions 924 may also reside, completely or at least partially, within the main memory 904, the static memory 906, and/or within the processor 902 during execution thereof by the computer system 900. The main memory 904 and the processor 902 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 924, or that which receives and executes instructions 924 from a propagated signal so that a device connected to a network environment 926 can send or receive voice, video or data, and to communicate over the network 926 using the instructions 924. The instructions 924 may further be transmitted or received over a network 926 via the network interface device 920.

While the machine-readable medium 922 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An apparatus, comprising:
an outer nozzle operable to discharge at an egress of the outer nozzle an outer stream at a first flow rate, the outer stream comprising a shell solution; and
an inner nozzle placed within the outer nozzle, wherein the inner nozzle is operable to discharge at an egress of the inner nozzle an inner stream at a second flow rate, the inner stream comprising a core solution intermixed with a plurality of materials,
wherein the outer stream substantially surrounds the inner stream, thereby forming a combined stream,
wherein a plurality of capsules are formed responsive to a force applied to the combined stream,
wherein at least a portion of the plurality of capsules are desirable capsules, each comprising a core encapsulated by a portion of the shell solution, and
wherein the core comprises at least one of the plurality of materials encapsulated by a portion of the core solution,
a sensing device to detect undesirable capsules using image recognition;
a charging device coupled to the sensing device, wherein the charging device recieves a signal from the sensing device responsive to the sensing device detecting the undesirable capsules, and wherein the charging device applies a bias only to the detected undesirable capsules responsive to receiving the signal from the sensing device; and a selection device to segregate the biased undesirable capsules from the unbiased desirable capsules.

2. The apparatus of claim 1, wherein the force comprises at least one of an acoustic force, an electrostatic force, and a fluid force.

3. The apparatus of claim 1, wherein a size and thickness of the plurality of capsules is controlled by at least one of the first and second flow rates, a diameter of each of the inner and out nozzles, an amplitude or a magnitude of the force applied on to the combined stream.

4. The apparatus of claim 1, wherein at least one of the shell solution and the core solution comprises a biocompatible material.

5. The apparatus of claim 4, wherein the biocompatible material corresponds to an alginate having a non-antigenic property that substantially prevents an immune response in a mammal.

6. The apparatus of claim 1, wherein the portion of the shell solution surrounding the core comprises one of a polymeric solution and an alginate solution.

7. The apparatus of claim 1, comprising a reservoir for receiving at least a portion of the plurality of capsules.

8. The apparatus of claim 7, comprising a power source to electrically charge the plurality of capsules and thereby prevent them from coalescing in the reservoir.

9. The apparatus of claim 7, wherein the reservoir comprises an additive to facilitate at least one of a gelation, crosslinking, and solidification of the plurality of capsules received by the reservoir.

10. The apparatus of claim 9, wherein the additive comprises one of an inorganic salt, and a polycation.

11. The apparatus of claim 9, wherein the reservoir is configured to provide an electrical potential to the additive to control charge build-up in the reservoir.

12. The apparatus of claim 1, wherein one of the inner stream and the outer stream comprises an imaging agent for tracing a portion of the plurality of capsules with imaging technology.

13. The apparatus of claim 12, wherein the imaging agent comprises one of a nanoparticle and a contrast agent.

14. The apparatus of claim 1, wherein the sensing device comprises an image sensor for facilitating a detection of one or more defective capsules in the plurality of capsules, wherein a defective capsule comprises one of a first capsule with a missing core, and a second capsule with one of the plurality of materials protruding from the shell solution encapsulating it.

15. The apparatus of claim 14, wherein the selection device comprises a first conductor for biasing the undesirable capsules and a second conductor for segregating the one or more undesirable capsules from the desirable capsules.

16. The apparatus of claim 15, comprising a controller to:
    detect from images supplied by the image sensor the desirable capsules and the one or more undesirable capsules; and
    direct the selection device to segregate the one or more undesirable capsules from the desirable capsules by charging the one or more undesirable capsules and repelling them from a path of the desirable capsules.

17. The apparatus of claim 1, wherein the plurality of materials correspond to a mammalian cell.

18. The apparatus of claim 17, wherein the mammalian cell corresponds to one of a human cell, a porcine cell, an ovine cell, and a bovine cell.

19. The apparatus of claim 18, wherein the human cell comprises one of a hepatocyte, a hormone producing cell, a stem cell, an inducible nitric oxide synthases (iNOS) expressing cell, a parathyroid cell, and a fibroblast cell.

20. The apparatus of claim 19, wherein the hormone producing cell corresponds to a pancreatic islet cell, and wherein the stem cell corresponds to a myoblastic cell.

* * * * *